US006756591B1

(12) United States Patent
Lounis et al.

(10) Patent No.: US 6,756,591 B1
(45) Date of Patent: Jun. 29, 2004

(54) METHOD AND DEVICE FOR PHOTOTHERMAL IMAGING TINY PARTICLES IMMERSED IN A GIVEN MEDIUM

(75) Inventors: Brahim Lounis, Bordeaux (FR); Michel Orrit, Pays Bas (FR); Philippe Tamarat, Gradignant (FR); David Boyer, Mont de Marsan (FR); Laurent Cognet, Bordeaux (FR)

(73) Assignees: Centre National de la Recherche, Paris (FR); Universite de Bordeaux I, Talence (FR)

( * ) Notice: Subject to any disclaimer, the term of this patent is extended or adjusted under 35 U.S.C. 154(b) by 0 days.

(21) Appl. No.: 10/388,238

(22) Filed: Mar. 14, 2003

(51) Int. Cl.$^7$ .............................. G30G 5/16; G01J 5/02; G01N 25/72; G01N 25/00
(52) U.S. Cl. .............................. 250/316.1; 250/339.14; 250/341.1; 250/341.2; 250/341.6; 250/345; 250/352; 250/358.1; 374/4; 374/5; 374/7; 374/20; 374/45; 374/57; 374/124; 374/126; 374/127; 374/128; 374/129; 374/130; 374/162
(58) Field of Search .................... 250/316.1, 339.14, 250/341.1, 341.2, 341.6, 345, 352, 358.1; 374/4, 5, 7, 20, 45, 57, 124, 126–130, 162

(56) References Cited

U.S. PATENT DOCUMENTS

| 3,655,256 A | * | 4/1972 | Claytor et al. ............... 430/1 |
| 4,000,334 A | * | 12/1976 | Hallman et al. ............ 430/348 |
| 4,468,136 A | * | 8/1984 | Murphy et al. ............... 374/45 |
| 4,513,384 A | * | 4/1985 | Rosencwaig ................ 702/170 |
| 4,950,897 A | * | 8/1990 | Mandelis et al. ........... 250/334 |
| 5,111,048 A | * | 5/1992 | Devitt et al. ................ 250/342 |
| 5,118,945 A | * | 6/1992 | Winschuh et al. ........ 250/341.4 |
| 5,365,065 A | * | 11/1994 | Power ......................... 250/330 |

(List continued on next page.)

OTHER PUBLICATIONS

Boyer et al; "Photothermal Imaging of Nanometer–Sized Metal Particles Among Scatterers"; Science (Washington, DC), vol. 297, No. 5584, 2002, pp. 1160–1163; XP002242687.

Beil et al; "Chromatin texture analysis in three–dimensional images from confocal scanning laser microscopy"; Analytical and Quantitative Cytology and Histology, vol. 17, No. 5, 1995, pp. 323–331, Abstract; XP002242688.

Bialkowski; "Using An Optical Novelty Filter To Enhance Contrast In Photothermal Refraction Spectrometry"; 10th International Conference on Photoacoustic and Photothermal Phenomena; Aug. 23–27, 1998; XP002242705.

(List continued on next page.)

*Primary Examiner*—John R Lee
*Assistant Examiner*—Bernard Souw
(74) *Attorney, Agent, or Firm*—Stite & Harbison, PLLC; Ross F. Hunt, Jr.

(57) ABSTRACT

A method and device for photothermal imaging tiny metal particles which are immersed in a given medium like a living cell deposited onto a transparent glass slide. The given medium and immersed tiny metal particles are illuminated through separate phase reference laser beam and sensitive probe laser beam, with the sensitive probe laser beam including a heating laser beam undergoing through impingement on the given medium slight phase changes induced by photothermal effect due to a local heating, in the absence of any substantial phase changes to the phase reference laser beam. Illuminating is performed by focusing the separate phase reference and sensitive probe laser beam through the transparent glass slide at a given depth within the given medium and a transmitted phase reference laser beam and a transmitted sensitive probe laser beam undergoing the slight phase changes are generated. An image of the given medium at the given depth is formed through the transmitted phase reference and sensitive probe laser beam and the slight phase changes on the transmitted sensitive probe laser beam with reference to the reference phase laser beam are detected so as to allow each of the tiny metal particles to be imaged as an optical label.

21 Claims, 8 Drawing Sheets

U.S. PATENT DOCUMENTS

| | | | | |
|---|---|---|---|---|
| 5,451,785 A | * | 9/1995 | Faris | 250/330 |
| 6,049,220 A | * | 4/2000 | Borden et al. | 324/765 |
| 6,080,988 A | * | 6/2000 | Ishizuya et al. | 250/338.1 |
| 6,103,351 A | * | 8/2000 | Ram et al. | 428/195.1 |
| 6,419,387 B1 | * | 7/2002 | Legrandjacques et al. | 374/5 |
| 2002/0126732 A1 | * | 9/2002 | Shakouri et al. | 374/130 |

OTHER PUBLICATIONS

Sheard et al.; "A new technique for imaging hard tissue by photothermal radiometric microscopy"; Scanning, vol. 11, No. 3, pp. 135–138; XP–002242689; Abstract.

Sönnichsen et al.; "Spectroscopy of single metallic nanoparticles using total internal reflection microscopy"; Applied Physics Letters, American Institute of Physics, vol. 77, No. 19; pp. 2949–2951, Nov. 6, 2000; XP–000970253.

Unknown; "Microscopic and spectroscopic imaging of the chemical state"; Practical Spectroscopy Series, vol. 16, p. Viii+495p; XP–002242690 Abstract.

* cited by examiner

METHOD AND DEVICE FOR PHOTOTHERMAL IMAGING TINY PARTICLES IMMERSED IN A GIVEN MEDIUM

The present invention relates generally to photothermal imaging tiny particles immersed in a given medium. More particularly the present invention relates to photothermal detection of metallic particles that can serve as a label for organelles or organic compounds and biomolecules included in a living cell.

Ambient optical detection of labeled molecules is presently limited to fluorescent dyes by photobleaching and semiconducting particles of nanometer size by blinking effects.

Nanometer-sized metal particles do not optically bleach and appear therefore particularly useful to serve as optical labels, provided suitable detection process can be found.

An ideal optical label for large molecules should generate an intense optical signal, be of very small size, prove durable in time, as well as chemically inert and easy to bind to the molecule of interest in a controlled manner.

All present-day known optical markers fall short of the ideal label status definition.

The most common known labels, like fluorescent dyes, can usually be grafted to the molecule of interest. Their red-shifted fluorescence can be sifted very efficiently out of the given background.

The main drawback they are known to suffer however is photobleaching, i.e. an irreversible photochemical process leading from the excited fluorophore status to a non-fluorescent product.

Nanocrystals of II–VI semi-conductors, such as CdSe/ZnS have recently been proposed as optical markers. See particularly M. Bruchez, Jr., M. Moronne, P. Gin, S. Weiss, A. P. Alivisatos, in Science 281, 2013–6 1998 and W. C. Chan, S. Nie, in Science 281, 2016–8, 1998.

Although the semi-conductors resist bleaching longer than dyes, their luminescence brightness is liable to blinking while they are difficult to functionalize in a controlled way.

In contradistincton, metal particles are known to be currently used for single-particle or single-molecule tracking and immocytochemistry, see as an example W. Baschong, J. M. Lucocq and J. Roth, Histochemistry 83, 409–11 (1985) or J. W. Slot and H. J. Geuze, Eur J. Cell Biol 38, 87–93 (1985).

The above mentioned metal particles can either take the form of colloids with diameters ranging between a micron and a few nanometers or synthesized clusters with well-defined chemical structures. See for example P. A. Frey and T. G. Frey. J Struct Biol 127, 94–100 (1999) or J. F. Hainfeld and R. D. Powell J Histochemistry Cytochemistry 48, 471–80 (2000).

Sub-micrometer metal particles down to diameters of 40 nm can be imaged using an optical microscope by means of their Rayleigh given, by illuminating in dark field at the plasmon frequency, with differential interference contrast (DIC) and video enhancement, or with total reflexion. See particularly S. Schultz, D. R. Smith, J. J. Mock and D. A. Schultz in Proc. Natl. Acad. Sci. USA 97, 996–1001 (2000), J. Gelles, B. J. Schnapp, M. P. Sheetz, in Nature 331, 450–3 (1988) and C. Sönnischen et al in Applied Physics Letters 77, 2949–2951 (2000) respectively for the three preceding mentioned alternatives.

While metal particles are very appealing optical labels owing to their absence of photobleaching phenomenon and optical saturation at reasonable exciting intensities, the Rayleigh given phenomenon they undergo decreases like the sixth power of their diameter, with the given signal being to be discriminated from a strong background.

Therefore the minimum size in diameter of a particle being detected in a living cell or in a given tissue is in practice well above the theoretical limit of 40 nm in diameter.

The well known Electron microscopy with its superior spatial resolution can well distinguish particles with diameters as low as 5 nm from organelles in a cell. See particularly J. M. Robinson, T. Takizawa, D. D. Vandre in J. Microscience 199, 163–79 (2000). Unfortunately Electron microscopy cannot be operative at ambient conditions.

The present invention provides for a method and device for photothermal imaging tiny metal particles immersed in a given medium particularly adapted to remedy the drawbacks suffered by the methods, processes and devices of the prior art.

The method and the device which are the object of the present invention distinguish over the method and device of the copending provisional application U.S. Ser. No. 60/410, 305 filed on Sep. 13, 2002, now filed as the complete specification U.S. Ser. No. 10/386,937 filed on Mar. 13, 2003 in that detecting the photothermal effect and corresponding induced phase changes takes place now with highly reduced illuminating power, without inducing any damage or detrimental effect to living bodies like cells whose organelles or tiny compounds elements can thus be submitted to fine labeling.

More particularly one object of the present invention is to provide for a method and device for photothermal imaging small particles, metal particles, down to 1 nm in diameter at ambient conditions with an optical microscope.

Another object of the present invention is thus to provide for a method and device for photothermal imaging small particles allowing thus to correlate single particle, as labels, with optical microscopic images, without any need for conjugation to bulky fluorescent antibodies.

Another object of the present invention is thus to provide for a very high sensitive method and device particularly adapted to allow an efficient, reproductible and promising way to visualize low amounts of proteins biomolecules or organelles in living cells or belonging to the membrane thereof.

According to the method for photothermal imaging tiny metal particles immersed in a given medium which is the object of the invention, the given medium is deposited on a transparent glass slide.

The given medium and immersed tiny particles are illuminated through separate phase reference laser beam and sensitive probe laser beam the sensitive probe laser beam undergoing through impingement on the given medium slight phase changes induced by photothermal effect due to a local heating within the given medium, in the absence of any substantial phase changes to the phase reference laser beam.

Illuminating is performed by focusing the separate phase reference laser beam and sensitive probe laser beam through the transparent glass slide at a given depth within the given medium from the output face of the transparent glass slide, transmitted phase reference laser beam and transmitted sensitive probe laser mean undergoing these slight phase changes induced by photothermal effect due to a local heating being thus generated.

An image of the given medium and tiny particles at the given depth through the transmitted phase reference laser beam and transmitted sensitive probe laser beam is formed.

The slight phase changes on the transmitted sensitive probe laser beam with reference to the transmitted phase reference laser beam are detected on the image through differential phase interference contrast phenomenon, with each of the tiny metal particles immersed in the given medium being imaged as an optical label.

The device for photothermal imaging of tiny metal particle immersed in a given medium which is the object of the invention comprises a unit for illuminating part of this given medium and immersed tiny particles through separate phase reference laser beam and sensitive probe laser beam, the transmitted sensitive probe laser beam undergoing through impingement of the sensitive probe laser beam on the given medium slight phase changes induced by photothermal effect due to a local heating within the given medium, in the absence of any substantial phase changes to the transmitted phase reference laser beam.

It further comprises a unit for detecting these slight phase changes on the transmitted sensitive probe laser beam with reference to the transmitted phase reference laser beam through a differential phase interference contrast phenomenon. A unit is provided for imaging each of the tiny metal particles immersed within the given medium as an optical label from the differential phase interference contrast phenomenon.

The objectives, advantages and particulars of the present invention will be understood by reading the following detailed description and accompanying drawings.

The following detailed description contains many particulars for the purposes of sole illustration. These specifics are given as exemplary details belonging to the scope of the invention.

Figure 1A:
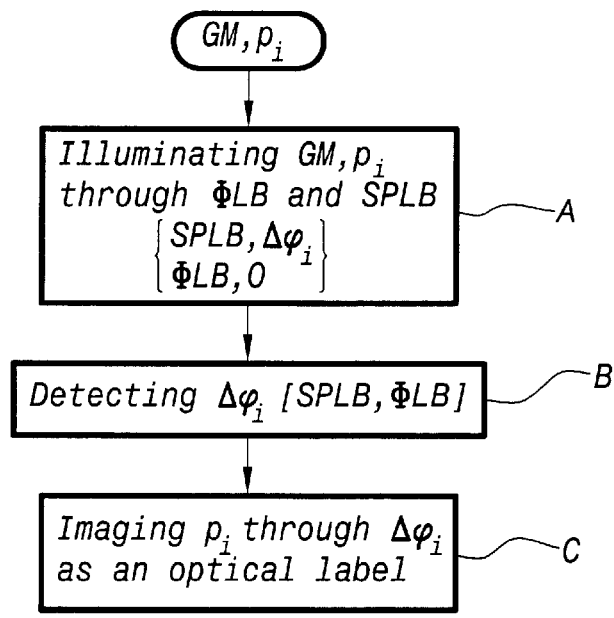
FIG. 1A shows a general flowchart of the method for photothermal imaging tiny metal particles immersed in a given medium according to the present invention.
Figure 1B:
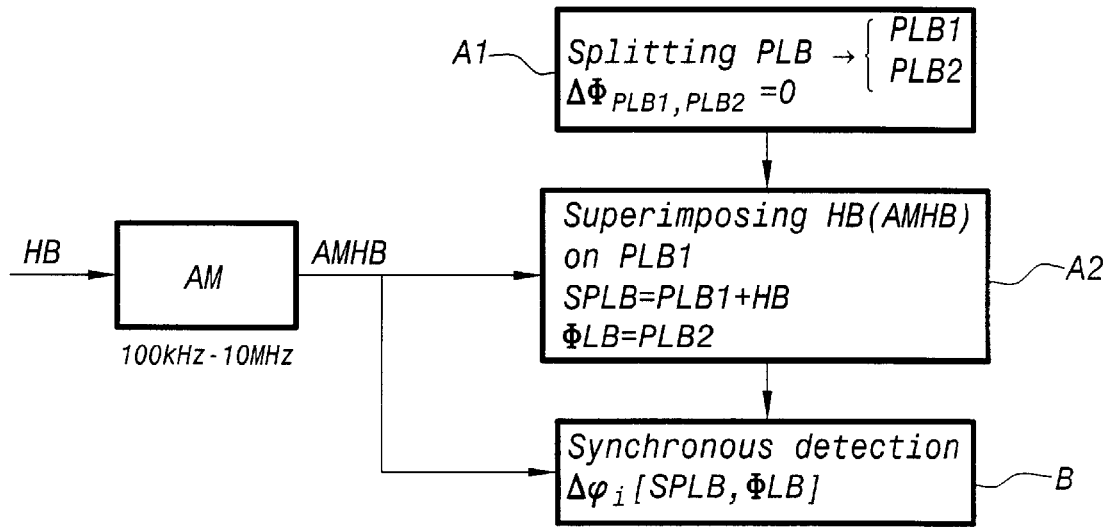
FIG. 1B shows particular embodiments of given steps of the method of the invention as shown at FIG. 1A.

The method for photothermal imaging tiny metal particles immersed in a given medium which is object of the invention is now disclosed in relation with FIGS. 1A and 1B.

As an example, the given medium in which the tiny particles are immersed into should be understood as a scattering medium or a non scattering medium including scatterers or the like.

As shown at FIG. 1A the method of the invention consists, in a step denoted A, in illuminating the given medium, which is denoted GM, and immersed tiny particles, denoted $p_i$, through separate phase reference laser beam denoted $\phi$LB and sensitive probe laser beam denoted SPLB.

As a consequence, the sensitive probe laser beam SPLB undergoes through impingement on the given medium GM slight phase changes induced by photothermal effect due to a local heating within this given medium GM, in the absence of any substantial phase changes to the phase reference laser beam $\phi$LB.

The phase relationship of each of the phase reference laser beam and sensitive probe laser beam is denoted SPLB, $\phi_i$ $\phi$LB, 0

With reference to FIG. 1A, step A is followed by a step denoted B consisting in detecting the slight phase changes on the sensitive probe laser beam SPLB, with respect to the phase reference laser beam $\phi$LB.

The detection of the slight phase changes can be conducted, according to one of the advantageous aspects of the method of the invention, through a differential phase interference contrast phenomenon.

The detection operation is illustrated by the following relationship $\phi_i$(SPLB, $\phi$LB)

From the preceding relationship it is understood that each slight phase changes induced by photothermal effect in the vicinity of each tiny metal particle $p_i$, with these slight phase changes being denoted $\phi_i$, is obtained thanks to the phase interference contrast phenomenon of both phase reference laser beam $\phi$LB and sensitive probe laser beam SPLB and thus detected.

Accordingly each of the tiny metal particles $p_i$ which are immersed in the given medium GM can thus be imaged as an optical label at step C shown at FIG. 1A.

The mode of operation of the method of the invention as disclosed in relation with FIG. 1A will be now justified on physical grounds below.

Because of the optical absorption of a small metal particle decreases as only the third power of its diameter, the absorption phenomenon will prevail over the given phenomenon below a given particle size.

The absorption cross section of a gold particle of 5 nm in diameter is about 3 $nm^2$ at 514 nm wavelength. This absorption value is more than two orders of magnitude greater than that of an organic fluorophore at room temperature.

Such a strong absorption value gives rise to a photothermal effect, i.e. a temperature rise around the particle when it is illuminated by a laser beam.

According to the method of the invention this temperature change is optically detected by a sensitive interference change akin to DIC (for differential interference contrast) with these particles being thus fully adapted to operate as optical labels.

A particular embodiment of the method of the invention, particularly its above mentioned steps A and B will be now disclosed with reference to FIG. 1B.

As shown at FIG. 1B, step A of illuminating the given medium GM and immersed tiny particles $p_i$ may consist at a sub-step A1 in splitting a probe laser beam, denoted PLB, into a first and a second probe laser, beam each denoted $PLB_1$ and $PLB_2$ respectively, with the first and second probe laser beam undergoing the same phase relationship on separate optical path.

The phase relationship between first and second probe laser beam is denoted $\phi_{PLB1,PLB2}=0$ Sub-step A1 is thus followed by a subsequent sub-step A2 consisting in superimposing on one or the first and second probe laser beam a heating laser beam, denoted HB, propagating on the same optical path as that of the first or second probe laser beam it is superimposed to. As an example, at sub-step A2 at FIG. 1B, the heating laser beam is superimposed on the first probe laser beam denoted $PLB_1$.

Consequently, the first probe laser beam $PLB_1$ and superimposed heating laser beam HB actually form the above mentioned sensitive probe laser beam SPLB, as already disclosed in relation with FIG. 1A. The second probe laser beam $PLB_2$ thus forms the phase reference laser beam $\phi LB$ as already disclosed in relation with FIG. 1A.

The operation of superimposing a heating laser beam HB to one of the probe laser beam, $PLB_1$, and assigning the second probe laser beam $PLB_2$ as phase reference laser beam $\phi LB$ is denoted through the relationship $SPLB=PLB_1+HB$ $\phi LB=PLB_2$.

With reference to FIG. 1B the step of detecting the slight phase changes step, denoted B at FIG. 1A, can be thus implemented preferably trough synchronous detection, as shown at step denoted B at FIG. 1B. To this end, the method of the invention may preferably consist in amplitude or intensity modulating the heating laser beam HB at a given frequency and thus synchronously detecting the slight phase changes through differential phase interference contrast phenomenon. The frequency for amplitude modulating the heating laser beam HB can be chosen in the range 100 kHz–10 MHz.

The above mentioned frequency can be chosen so that a given volume of the given medium overlaps the focal spot of the sensitive probe laser beam SPLB focused on the given medium.

The mode of operation of the method of the invention as shown at FIG. 1B will be now justified below.

While photothermal detection is fully known from the prior art particularly using a thermal lens effect to detect very low concentrations of absorbing molecules in liquid solutions, the method of the invention, as illustrated at FIG. 1B, makes use of a very sensitive polarization interference method which allows the detection of slight phase changes. A full description of such a method has been published by P. Cleizes, A. C. Boccara, and H. Saint-James, in optic letters 22 (1529–1531 99 97).

Introducing further an amplitude modulation of the heating laser beam HB and then a synchronous detection of the small phase changes induced through photothermal effect on the sensitive probe laser beam SPLB allows hence to improve the noise rejection by means of the high frequency modulation.

The volume undergoing a significant temperature modulation is determined by the dumping of heat waves at the modulation frequency. Consequently, the frequency for amplitude modulation is thus chosen such that this volume overlapses the focal spot of the sensitive probe laser beam SPLB.

The photothermal contrast can thus be implemented on a standard optical microscope, such a mode of operation being used with organic or biological samples in a given medium, without introducing negligible background.

Figure 2A:
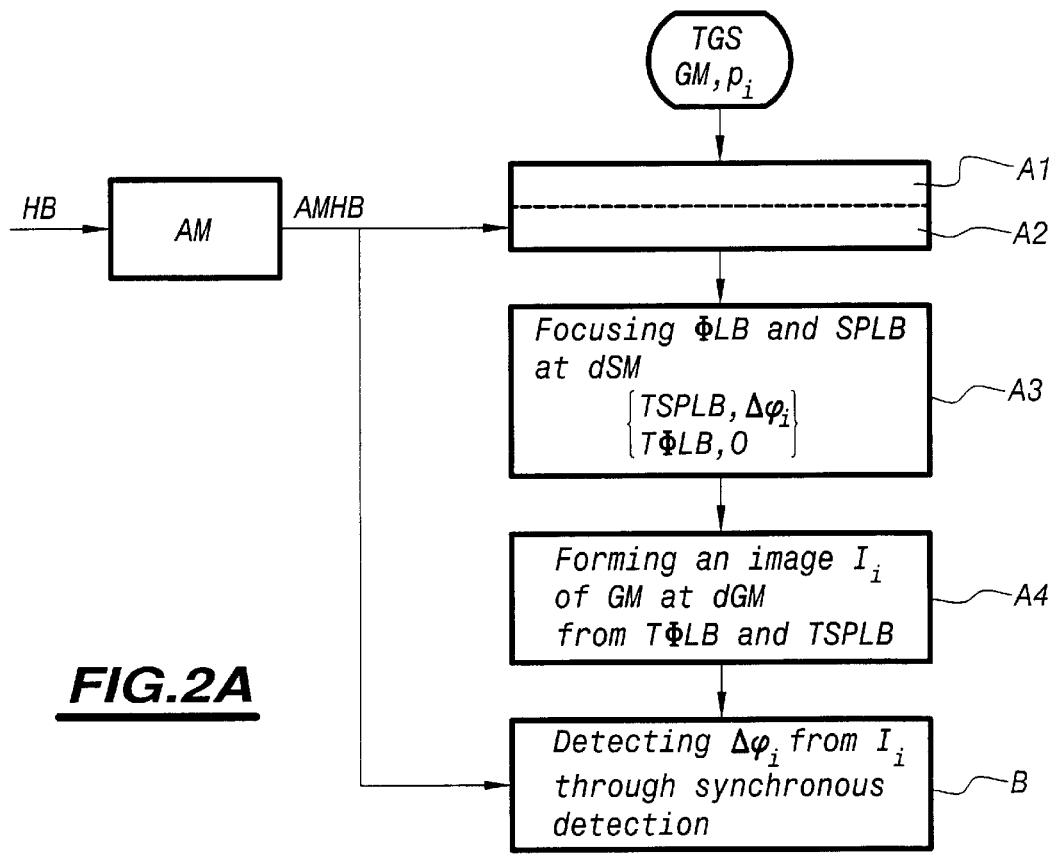
FIGS. 2A to 2C show exemplary embodiments of the method according to the invention, in which the phase changes detection is performed on transmitted phase reference and sensing probe laser beam after transmission through the given medium.
Figure 2B:
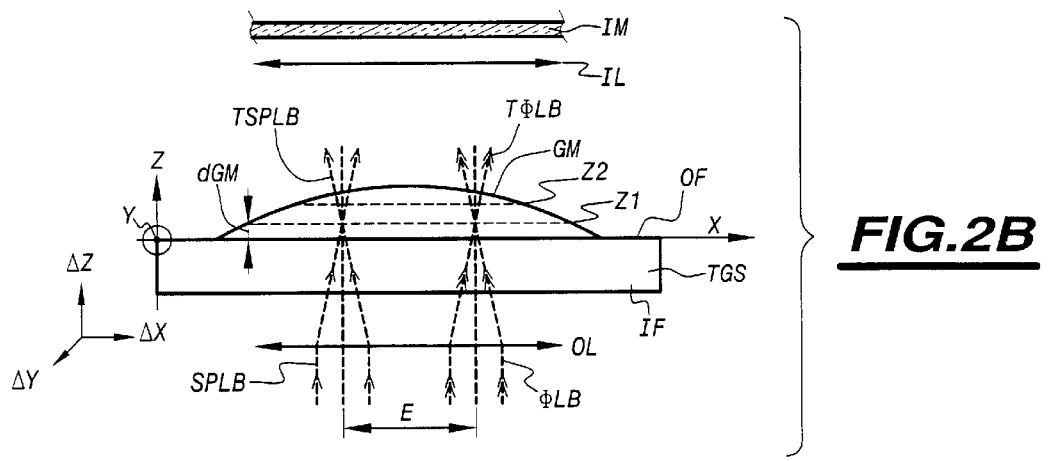
Figure 2C:
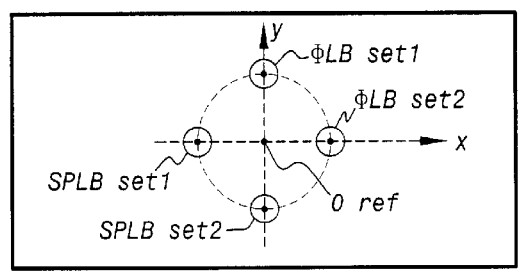

A particular embodiment of the method of the invention will now be disclosed with reference to FIGS. 2A to 2C in which the phase changes detection is performed on transmitted phase reference and sensing probe laser beam after transmission through the given medium GM.

With reference to FIG. 2A it is thus considered that the given medium GM is now deposited on a transparent glass slide, denoted TGS.

As shown at FIG. 2A, the method of the invention comprises the sub-step $A_2$ already disclosed with reference to FIG. 1B.

More particularly the method of the invention consists, in a step denoted $A_3$, in focusing a separate phase reference laser beam $\phi LB$ and sensitive probe laser beam SPLB through the transparent glass slide TGS at given depth within the given medium SM. As an example, the given depth is denoted dGM with this depth being defined from the output face OF of the transparent glass slide TGS where the given medium is deposited on.

Focusing the separate phase reference laser beam and sensitive probe laser beam this way allows to illuminating the given medium GM and tiny metal particles $p_i$ at the given depth dGM while a transmitted phase reference laser beam and a transmitted sensitive probe laser beam respectively denoted TSPLB and T$\phi$LB are thus generated.

As previously mentioned within the present specification the transmitted sensitive probe laser beam TSPLB undergoes the slight phase changes induced by photothermal effect due to local heating in the absence of any corresponding slight phase changes to the transmitted phase reference laser beam T$\phi$LB.

Generating the transmitted sensitive probe laser beam and corresponding slight phase changes $\phi_i$ together with the transmitted phase reference laser beam T$\phi$LB in the absence of any phase changes is denoted through the relationship TSPLB, $\phi_i$ T$\phi$LB, 0.

Sub-step $A_3$ is thus followed by a subsequent sub-step $A_4$ consisting in forming an image of the given medium GM and tiny particles at the given depth dGM, thanks to the transmitted phase reference laser beam T$\phi$LB and the sensitive probe laser beam TSPLB. This image is denoted $I_i$ at sub-step A4.

Sub-step $A_4$ can be thus followed by the step B or FIG. 1B, for example, in which detecting of the slight phase changes on the transmitted sensitive probe laser beam with reference to the transmitted phase reference laser beam is performed on the image $I_i$.

At FIG. 2B we have shown the physical operation of focusing the separate phase reference laser beam and sensitive probe laser beam through the transparent glass slide TGS at the given depth dGM.

In this situation, the phase reference laser beam and sensitive probe laser beam are considered to be focused at a given depth dGM equal to a value $Z_1$ with respect to the output face of the transparent glass slide TGS.

Focusing the separate phase reference laser beam and sensitive probe laser beam as shown at FIG. 2B at the given depth dGM can be obtained thanks to an objective lens denoted OL in a well-known manner while forming an image $I_i$ can also be obtained thanks to an image lens IL as shown at FIG. 2B.

The detection of the slight phase changes on the image $I_i$ can be performed on the image projected to a detector as an example as it will be disclosed in more details in the subsequent description relating to the device of the invention.

In order to avoid using bulky optical equipment downstreams the transparent glass slide TGS and given medium GM, the method of the invention as shown at FIGS. 2A and 2B may also consist in retro-reflecting the image $I_i$ and transmitted sensitive probe laser beam and phase reference laser beam forming such an image and recombining the thus retro-reflected transmitted phase reference laser beam T$\phi$LB and sensitive probe laser beam TSPLB to a unique sensing laser beam, in which the differential phase interference phenomenon is induced.

By recombining the retro-reflected transmitted phase reference laser beam and sensitive probe laser beam to a unique sensing laser beam undergoing the differential phase interference phenomenon, it should be understood that such a recombination allows the above mentioned retro-reflected laser beam to propagate along the same optical path as that of the sensitive probe laser beam and phase reference laser beam, and thus as that of the first and second sensitive probe laser beam so as to reduce the amount of bulky optical components, which are necessary to perform the detection operation as this will be disclosed in more details later in the specification.

With reference to FIG. 2B, the operation of retro-reflecting the image $I_i$ and transmitted sensitive probe laser beam and phase reference laser beam forming this image can be performed through an image mirror, denoted IM, which is placed and adapted to retro-reflect the transmitted sensitive probe laser beam and phase reference laser beam, as shown at FIG. 2B.

Particular embodiments of the method of the invention will be now disclosed with respect to FIGS. 2B and 2C.

With reference to FIG. 2A the sub-step $A_3$ of focusing the separate phase reference laser beam and sensitive probe laser beam can be performed by successive shifting increments along two reference directions parallel to the output face OF of the transparent glass slide TGS, with the focusing of these laser beams taking place at a same given depth within the given medium GM.

At FIG. 2B we have shown the two reference directions X and Y which are parallel to the output face OF of the transparent glass slide TGS, with the focusing of the laser beam taking place at a given depth dGM=$Z_1$ as illustrated at FIG. 2B.

It should thus be understood that a true dimensional imaging of the given medium GM and tiny particles $p_i$ immersed therein at the given depth dGM can thus be obtained from an adequate scanning of the whole surface of the given medium, by successive shifting increments $\Delta X$ and $\Delta Y$ as shown at FIG. 2B.

FIG. 2C is a downside view of FIG. 2B, i.e. a view of the input face IF of the transparent glass slide TGS which is illuminated by one or more laser beams.

With reference to FIG. 2C, the sub-step of focusing the separate phase reference laser beam and sensitive probe laser beam at a given depth is preferably performed by successive depth increments through the output face OF of the transparent glass slide TGS, with this depth increments being denoted $\Delta Z$.

Operating the method of the invention as disclosed with reference to FIG. 2B allows thus a sliced imaging of the given medium SM and tiny particles $p_i$ at successive intermediate depths $Z_1$, $Z_2$ and subsequent ones to be obtained by scanning along the orthogonal reference direction OZ, as shown at FIG. 2B.

A preferred embodiment of the method of the invention is now disclosed with reference to FIG. 2C such an embodiment allowing the diffusion movement of organelles of a living cell to be located with respect to a given reference origin with a very high degree of accuracy.

To this end the substep of focusing the phase reference laser beam and sensitive probe laser beam, i.e. sub-step $A_3$ of FIG. 2A, may include focusing at least a first and a second set of phase reference laser beam and sensitive probe laser beam, with these sets being denoted set 1 respectively set 2 at FIG. 2C.

As shown at FIG. 2C, the beam center of the laser beams of the first and second set of phase reference and sensitive probe laser beam are oriented so as to define a first and a second local reference directions denoted –x–y.

The first and second reference directions cross one another at a reference point taken as origin and thus denoted $O_{ref}$ as shown at FIG. 2C.

Any tiny particle can thus be imaged and located with respect to the first and second reference directions and more particularly to their common origin $O_{ref}$.

It should thus be understood that combining the mode of operation of the method of the invention, as shown at FIGS. 2B and 2C, allows thus to perform a tracking of any given tiny particle with respect to the reference directions and their common origin while the tiny particle under consideration is submitted to a diffusion or convection phenomenon or the like within the given medium GM.

More particularly focusing on the input face IF of the transparent glass slide a plurality of sets of phase reference laser beam and sensitive probe laser beam so as to form an array of reference directions and common origins will be considered as a variation within the scope of the present invention to any person of ordinary skill in the corresponding art.

More particularly with reference to FIG. 2C the heating laser beam HB which is superimposed on one of the first and second probe laser beam forming the sensitive probe laser beam of each of the first and second set or subsequent one of phase reference and sensitive probe laser beam can be lightly defocused so as to substantially cover the central area of the given medium GM lying between the phase reference and sensitive probe laser beam forming the first and second set as shown in phantom line at FIG. 2C.

It is thus emphasized that the method of the invention as previously disclosed with reference to FIGS. 2A to 2C is of uttermost interest to perform fluorescent imaging of cell culture, of transfected COS7 cells and immunostaining, immunohystochemistry and more generally labeling organelles and/or compounds medium like biomolecules within a living cell, as it will be explained in more details later in the specification.

Figure 3:
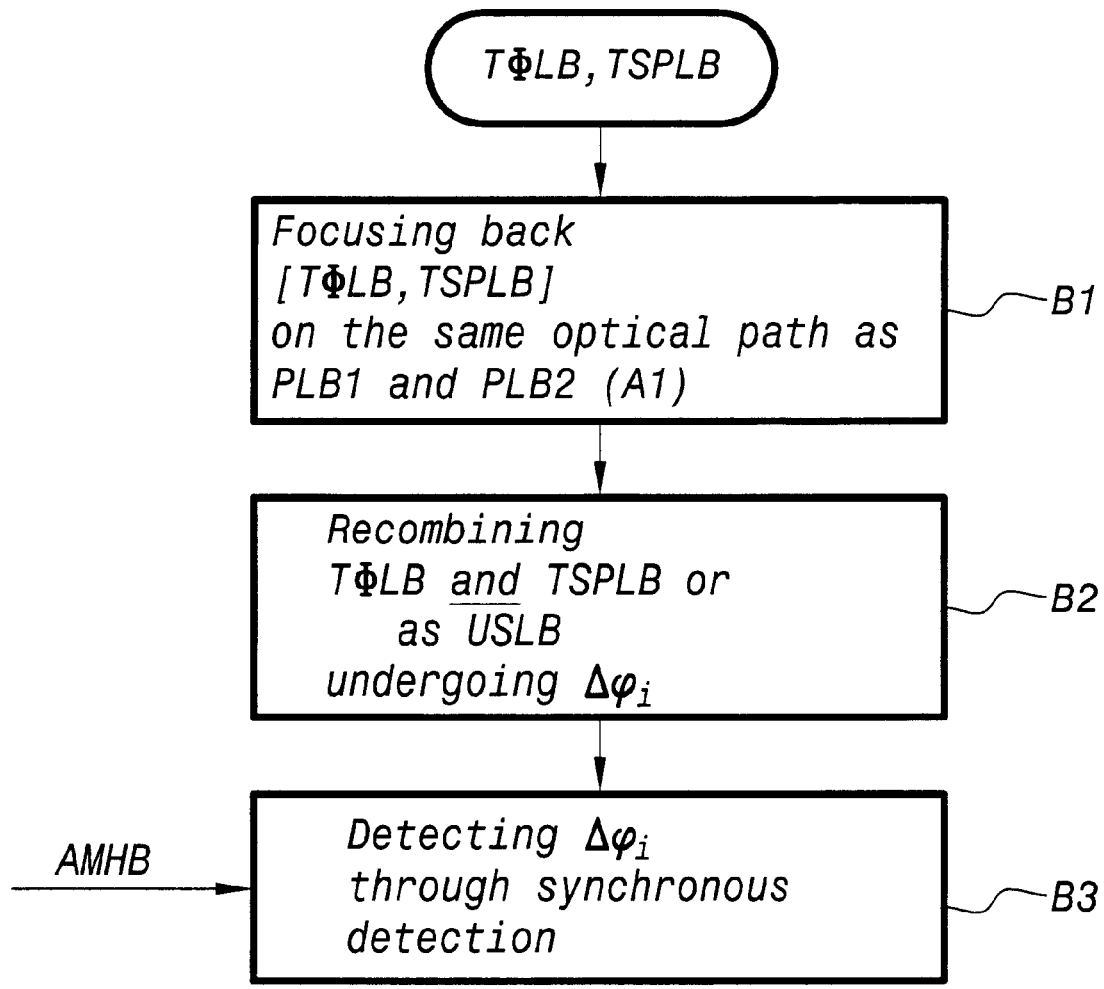
FIG. 3 shows a particular exemplary embodiment of the method of the invention in which a common processing of the transmitted phase reference and sensing probe laser beam shown at FIGS. 2A to 2C is disclosed.

A particular mode of operation of the method of the invention will be now disclosed with reference to FIG. 3.

As shown at FIG. 3 the method of the invention may consist at a step $B_1$ in focusing back the retro-reflected transmitted phase reference laser beam and transmitted sensitive probe laser beam, denoted T$\phi$LB, TSPLB, on the same optical path as that of the first and second probe laser beam $PLB_1$ and $PLB_2$, as already disclosed in relation to sub-step A1 of FIG. 2A.

Sub-step B1 is thus followed by a sub-step B2 consisting in recombining the focused reflected phase reference and reflected sensitive probe laser beam for retro-reflected transmitted phase laser beam and transmitted sensitive probe laser beam to a unique sensing laser beam denoted USLB in which the differential phase interference phenomenon $\phi i$ is induced.

The recombination operation is denoted
recombining
T$\phi$LB and TSPLB
to USLB undergoing $\phi_i$.

Figure 4:
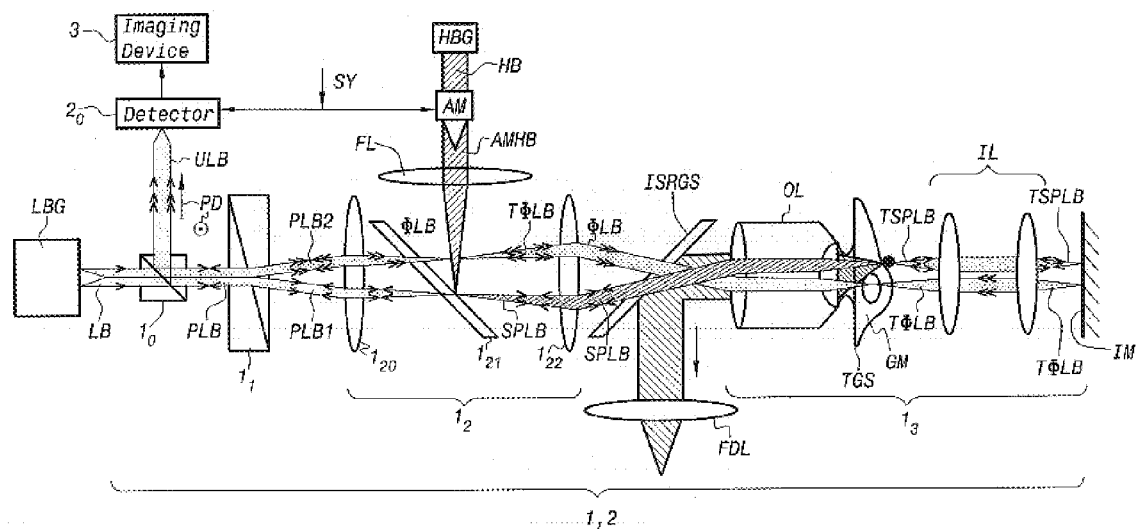
FIG. 4 shows a general view of a device for photothermal imaging tiny metal particles immersed in a given medium according to a preferred embodiment of the present invention, this device being more particularly adapted to operating the method of the invention as shown at FIGS. 1A, 1B and 2A to 2C.

A fully detailed description of a preferred embodiment of a device for photothermal imaging, tiny metal particles immersed in a given medium according to the invention is now given with reference to FIG. 4.

With reference to the abovementioned FIG. 4, the device of the invention comprises a unit 1 for illuminating part of the given medium denoted GM and immersed tiny particles $p_i$, through separate phase reference laser beam and sensitive probe laser beam denoted $\phi$LB and SPLB respectively. The sensitive probe laser beam undergoes through impingement on the given medium GM slight phase changes induced by photo thermal effect due to local heating within the given medium in the absence of any substantial phase changes to the phase reference laser beam $\phi$LB as already disclosed in the present description.

As shown at FIG. 4, the device of the invention also includes a unit 2 for detecting the slight phase changes on the sensitive probe laser beam, this detecting unit being denoted 2 and adapted to perform a detection through a differential phase interference contrast phenomenon, with reference to the phase reference laser beam $\phi$LB.

According to a particular advantaging feature of the device of the invention, the unit 1 for illuminating and the unit 2 for detecting may substantially comprise the same optical components, as it will be disclosed in more details later on in the description.

A unit 3 for imaging each of the tiny metal particles $p_i$ immersed in the given medium GM as an optical label is provided with the imaging being performed from the differential phase interference contrast phenomenon.

As shown on FIG. 4, the unit 1 for illuminating may comprise a laser beam generator denoted LBG adapted to generate a laser beam LB. The laser generator LBG may consist of an He—Ne laser generator at a 633 nm wavelength. The generated laser beam LB is polarised horizontally with a polarisation direction PD of the probe laser beam PLB shown on FIG. 4 as orthogonal to this figure. Polarisation takes place through a polarizing cube denoted $1_0$, with the probe laser beam PLB being understood as a polarised probe laser beam.

The unit 1 for illuminating further comprises a sub-unit for splitting the probe laser beam PLB to a first and second probe laser beam, denoted $PLB_1$ and $PLB_2$, with the first and second probe laser beam undergoing the same phase relationship on separate optical paths as shown on FIG. 4. Preferably, the sub-unit for splitting $1_1$ may consist of a Wollaston prism.

The unit 1 for illuminating further comprises a heating laser beam generating unit denoted HBG adapted to generating a heating laser beam denoted HB. The heating laser beam generating unit may consist of a laser generating unit at 514 nm wavelength delivering the heating laser beam HB to a further sub-unit for amplitude modulating the heating laser beam HB. On FIG. 4, the amplitude modulating unit is denoted AM. The amplitude or intensity modulating unit AM may consist of an electro-optic or acousto-optic modulator synchronised through a synchronising signal SY. The amplitude of intensity modulation may take place at high frequency, preferably in the range 100 kHz–10 MHz.

The unit 1 for illuminating as shown on FIG. 4 is further provided with a sub-unit denoted $1_2$ for superimposing the heating laser beam, particularly the amplitude modulated heating laser beam AMHB on one of the first and second probe laser beam $PLB_1$ or $PLB_2$.

As shown on FIG. 4, as a non limitative example, superimposing of the heating laser beam AMHB takes place on the first probe laser beam $PLB_1$ with a superimposed heating laser beam propagating thus on the same optical path as that of the first probe laser beam $PLB_1$.

The superimposed heating laser beam AMHB and the first probe laser beam $PLB_1$ propagates thus on the same optical path so as to constitute the sensitive probe laser beam denoted SPLB white the other one of the first and second probe laser beam, actually the second probe laser beam $PLB_2$, constituting thus the phase reference laser beam $\phi$LB.

As shown on FIG. 4, sub-unit $1_2$ for superimposing may consist of a focusing length denoted FL, adapted to focusing the amplitude modulated heating laser beam AMHB, together with a telecentric system which can be formed thanks to a first lens denoted $1_{20}$, a semi reflecting glass slide denoted $1_{21}$ and a second lens denoted $1_{22}$. As shown on FIG. 4, the heating laser beam and the first probe laser beam $PLB_1$ are focused on the same area of the output phase of the semi reflecting glass slide $1_{21}$, such a feature allowing thus the superimposing operation of both laser beams to be performed. Sub-unit $1_2$ preferably consists of a telecentric system.

According to a preferred embodiment of the device of the invention as shown at FIG. 4, sub-units $1_1$ and $1_2$, i.e. the Wollaston prism and the telecentric system, can be advantageously replaced by a unique Nomarski prism.

As it will be understood from FIG. 4, the unit 1 for illuminating further comprises a sub-unit $1_3$ adapted to focusing the phase reference laser beam $\phi$LB and the sensitive probe laser beam SPLB at separate locations on the given medium GM as shown on FIG. 4.

With reference to FIG. 2B for example, the separate locations at which both preceding laser beams are focused, should be understood as focusing points separated by a distance denoted E, with this distance allowing the phase reference laser beam $\phi$LB not to undergo the local heating generated by the sensitive probe laser beam SPLB and thus the slight phase changes induced on the latter.

As shown on FIG. 4, the sub-unit $1_3$ for focusing may consist of an inverted microscope equipped, as an example, with a 100× oil immersion objective of refractive index NA=1.4.

The preferred embodiment of the device of the invention as shown on FIG. 4 is more particularly adapted to allow the phase changes detection to be performed on transmitted phase reference laser beam and sensitive probe laser beam denoted T$\phi$LB and TSPLB respectively. With these transmitted laser beams being transmitted through the transparent glass slide TGS and by the given medium GM.

To that end, the device of the invention as shown on FIG. 4, comprises preferably a three D moving table in given reference directions, two of the reference directions, particularly directions X and Y as shown on FIG. 2B, being substantially parallel to the input face IF of the transparent glass slide TGS and the third one of the reference directions, i.e. direction Z, being substantially perpendicular to the input IF and output OF faces of the transparent glass slide. The objective lens OL thus mounted on the 3D moving table are thus adapted to focusing the separate reference laser beam PLB and sensitive probe laser beam SPLB through the transparent glass slide TGS at a given point at a depth dGM within the given medium with reference to the output phase OF of the transparent glass slide.

Generally, the 3D moving table may consist of a piezoelectric moving table with 3 independent degrees of liberty along the above-mentioned reference directions.

A focusing sub-unit is provided downstream the transmitted phase reference laser beam and sensitive probe laser beam with this focusing sub-unit being denoted as IL, standing for imaging lens, and preferably consisting of a condenser of NA=0.5

While the focusing sub-unit IL might well allow to form an image of the given medium GM and tiny particles $p_i$ at the given depth dGM from the transmitted phase reference laser beam and sensitive probe laser beam undergoing the slight phase changes induced by photo thermal effect with these transmitted laser beams emerging from this given medium, operating the detection of this light phase changes would afterwards imply recombining the transmitted sensitive probe laser beam TSPLB and transmitted phase reference phase laser beam TφLB so as to induce the differential phase interference phase phenomenon.

Operating this way would thus imply providing bulky and costly optical equipments adapted to recombine the above-mentioned laser beams.

To remedy the above-mentioned drawback, according to one of the features of interest of the invention, all the components and sub-units embodying the illuminating unit 1 are thus adapted to partially serve as the detecting unit 2 as previously mentioned in the description.

To that end, as shown on FIG. 4, the focusing unit $1_3$ is adapted to retro-reflecting the image $I_i$ formed by the imaging lens or condenser IL.

An image mirror IM is thus provided downstream the imaging lens IL, with this imaging mirror IM being adapted to retro-reflecting or reflecting back the transmitted sensitive probe laser beam TSPLB and transmitted phase reference laser beam TφLB along corresponding optical paths of the sensitive probe laser beam and phase reference laser beam illuminating the given medium. It should be understood on the light of FIG. 4 that the whole system formed by the imaging lens IL, the given medium GM, the transparent glass slide TGS and the objective lens OL are adapted to allow a corresponding retro-reflecting of the transmitted phase laser beam and sensitive probe laser beam along the same optical paths as that of impinging phase laser beam and sensitive probe laser beam respectively.

In the same way, sub-unit $1_2$ for combining, sub-unit $1_1$ for splitting and sub-unit $1_0$ for polarising embodying the illuminating unit 1 are fully adapted to constitute a recombining sub-unit allowing the retro-reflected phase reference and sensitive probe laser beam to a unique laser beam denoted ULB in which the differential phase interference phenomenon is induced.

As shown on FIG. 4, the unique laser beam ULB after recombination, reflection and transmission by the polarising cube or sub-unit $1_0$ is vertically polarised and thus sent to a detecting unit or detector $2_0$. The detecting unit $2_0$ may consist of a fast photo diode for instance. Detection can take place under control of the synchronising signal SY in order to allow a synchronous detection to be performed.

The detecting unit $2_0$ is thus connected to the imaging device 3 thus to allow a full imaging of the given medium GM and tiny metal particles immersed in this medium.

A fluorescence detecting lens denoted FDL may be added between sub-unit $1_2$ forming the telecentric system and the objective lens OL to allow comparative and/or supplementary fluorescence imaging of the given medium GM through an intermediate semi-reflecting glass slide denoted ISRGS, as shown at FIG. 4.

The mode of operation of the detecting unit $2_0$ can be summarised as follows;

The amplitude modulated heating laser beam AMHB induces a periodic phase difference between the transmitted sensitive probe laser beam and transmitted phase reference laser beam which gives rise to a modulation of the detected red intensity.

While the probe laser beam PLB is generated in the red domain of wavelength, the heating laser beam belongs to the range of the green wavelength.

Consequently, a red path filter can be used to eliminate green stray light from the heating beam. A locking amplifier can thus detect the variations of the red intensity and thus the dephasing between the retro-reflected transmitted sensitive probe laser beam and transmitted phase reference laser beam as the modulation frequency of the heating laser beam. The lock-in detection can thus be performed at the modulation frequency so as to perform the synchronous detection with an integration time of 10 milliseconds for example. Microscopic images are thus obtained thanks to the imaging device 3 by scanning the sample of given medium with the focused laser beam and sensitive probe laser beam or plurality of sets of these laser beams.

The embodiment of the device of the invention disclosed within the copending U.S. provisional patent application No. 60/410,305, in contradistinction to that as shown on FIG. 4, needs an illuminating power at each spot at which the phase reference laser beam and sensitive probe laser beam in red light to about 2.5 mW while the maximum power reaching the fast photo diode is only about 150 microwatts.

Several physical relationships common to the mode of operation of the preferred embodiment of the device of the invention and corresponding methods thereof will be given below. The elevation to temperature T caused at a distance r of a modulated point source of heat with power P[1+cos (ωt)] in a homogenous medium is derived from the equation of heat conduction and is given by:

$$T - T_0 = \frac{P}{4\pi\kappa r}[1 + \exp(-r/R)\cos(\varpi t - r/R)] \tag{1}$$

where $T_0$ is the ambient temperature, κ is the thermal conductivity of the medium and R is the characteristic length for heat diffusion at frequency ω given as $$\sqrt{2\kappa/\varpi C}$$

(C is the heat capacity of a unit volume of the medium). The phase difference between the two red beams embodying the phase reference laser beam and sensitive probe laser beam is proportional to the temperature change averaged over the spot size. The signal should be roughly constant for frequencies $\omega > \omega_s = 2\kappa C^{-1} R_s^{-2}$ (such that R is larger that the spot size $R_s$), and should decrease for $\omega > \omega s$. Typical values for the heat diffusion constant of organic materials lead to $\omega_s$ values around 1 MHz.

Samples were prepared by spin-coating a drop of an aqueous solution of poly-vynil-alcohol (PVA, 1% weight) doped with gold nanoparticles, on a microscope cover slip. The gold particles had diameters of 20, 10 and 5 nm with half-maximum dispersions in diameters of 2, 1 and 0.6 nm, respectively, according to the manufacturer's specifications. The three-dimensional representation of a photothermal image of 5-nm diameter gold nanoparticules has shown no background from the substrate, which means that the signal arises from the only absorbing objects in the sample, namely the gold nanospheres. These small nanoparticles were detected with a remarkably large signal-to-noise ration (S/N>10). Smaller particles with 2.4 nm diameter with a S/N~2 can be thus imaged. A histogram of peak heights for about 200 imaged spots has shown a fairly narrow unimodal distribution (in good agreement with the manufacturer's specifications), which clearly confirmed that the spots stem from individual nanospheres. Stronger peaks that could have been attributed to pairs of particles or to higher order aggregates were extremely rare. Any weaker spots even at a much higher heating power could not be found.

Further trials have shown that the imaging mechanism is indeed photothermal by determining the dependance of the signal with the particle size and the heating laser power. The signal intensities for 5, 10, and 20 nm diameter spheres varied linearly with the volume of the particles. This signal is perfectly linear in the heating power with no sign of saturation in the range of intensities which were used in the experiments (up to 20 MW/cm2 for the smallest spheres). A rough calculation of the temperature increase of the 5-nm spheres for this power gave about 15 K at the surface of the sphere, a temperature increase for which no significant change in optical properties did occur.

Investigation on how the signal depends on the distance between the green and red spots have also been conducted. Equation 1 predicts a signal decreasing as the inverse square of the distance, at large enough distances. The decrease that has been observed was indeed steeper that 1/r, although the distance range was too narrow to determine the exponent. As expected, however, the signal was largest when the green spot of the heating laser beam overlapped one of the red spots and presented a dispersion-like shape when the green spot was exactly in the middle of the phase reference and sensitive probe laser beam. The dependence of the signal as a function of the modulation frequency showed the expected decrease of the signal with frequency, in full agreement with numerical simulations based on the heat diffusion.

Comparative experiments between ordinary DIC imaging of scatterers like latex spheres with 300 nm diameter compared with gold nanoparticles with 80 nm and 10 nm in diameter have shown that only absorbing objects with high saturation intensities will appear in the photothermal image under our present conditions. In biological samples in particular, the absorption background from fluorescent labeling or from absorbing biomolecules appears to be utterly negligible.

The photothermal detection of small absorbing labels, being based on different principles, it presents definite advantages over fluorescence. The method and mode of operation of the devices of the invention is background-free, even in given environments. There is neither photobleaching, nor saturation for illumination intensities up to several tens of MW/cm². To the knowledge of inventors, no other optical method, not even near-field optics appears to be able to detect non-fluorescing objects as small as 2.5 nm. This represents a gain of more than three orders of magnitude in volume over the current optical detection by plasmon Rayleigh given.

In the present experiments, the temperature rise of metal particles with 5 nm diameter has been estimated to about 15 K. Because the temperature rise falls off as the reciprocal distance from the particle's center, it decreases to 3 K 13 nm away from the center. Although small, this temperature rise might still be too high for some proteins or biomolecules. However, it is believed that S/N can be significantly improved in a transmission geometry and by reaching the photon noise in detecting the sensitive probe laser beams. The label heating is hence expected to be reduced by a factor of 10, and would become negligible for most biomolecules at ambient conditions.

Corresponding results of significant experiments obtained by using the method and device of the invention with the phase difference interference phenomenon detection being performed on the transmitted sensitive probe and phase reference laser beam as already disclosed with reference to FIGS. 2A to 2C and 4 respectively are now reported.

Cell Culture, Transfection of COS7 Cells and Immunostaining

Specific experiments have been conducted on transfected COS7 cells.

COS7 cells were cultured plated on glass slides in DMEM medium supplemented with (100 Cg/ml) penicillium (100 $\mu$/ml) and 10% bovine serums in a humidified atmosphere (95%) at 5% $CO_2$ and 37°. Cells were used for 12–14 passages and were transferred every 4 days. Transfection was performed using FUGEN. Cells exhibiting confluence of about 30% were used for transfection with 10 $\mu$g of cDNA in a 1 ml volume coding for a metabotropic receptor for glutamate containing of myc-tag (mGluR5-myc). Transfection efficiency was reaching a 50% level. After 12 hours, the cells were fixed according to the following protocol: 10 minutes in paraformaldehide with 4% sucrose, 15 minutes in phosphate saline buffer (PBS) with 50 nM NH4Cl, then 3 rinses in PBS with 0.3% Bovine Serum Albumine (BSA). Then, a first immunostaining was performed using antimyc antibodies tagged with alexa 568 dyes (herein named amyc-Alexa568) (20 minutes at room temperature 10 $\mu$g/ml, 0.3% BSA). After two rinses in PBS, a second immunostaining by antiIgG-10 nm gold (Auroprobes Amersham, 20 minutes at room temperature, 0.3% BSA) was performed for different concentrations (10 $\mu$g/ml to 0.1 $\mu$g/ml) followed by 3 rinses in PBS.

Fluorescence Imaging

Fluorescence images were recorded with the heating laser beam HB at reduced powers, about 10$\mu$ W. The fluorescence was collected via the objective and filtered using a high pass filter, OG550, and imaged on a 500 $\mu$m size single photon counting avalanche photodiode. Since no pinhole was inserted in the fluorescence path, the fluorescence set-up was not confocal.

RESULTS AND DISCUSSIONS

Resolution

Figure 5A:
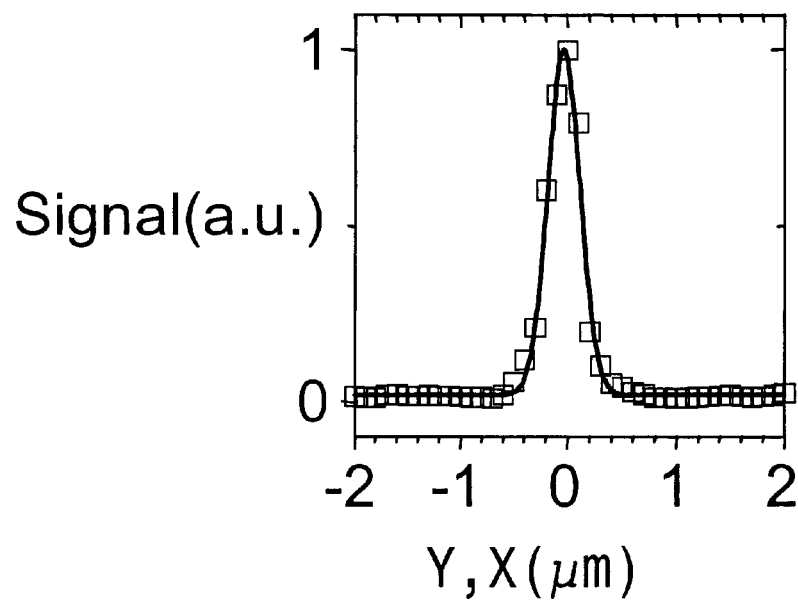
FIGS. 5A and 5B show diagrams illustrating the transverse, X and Y directions, and axial, Z direction, resolution of the method and device which are the object of the present invention.
Figure 5B:
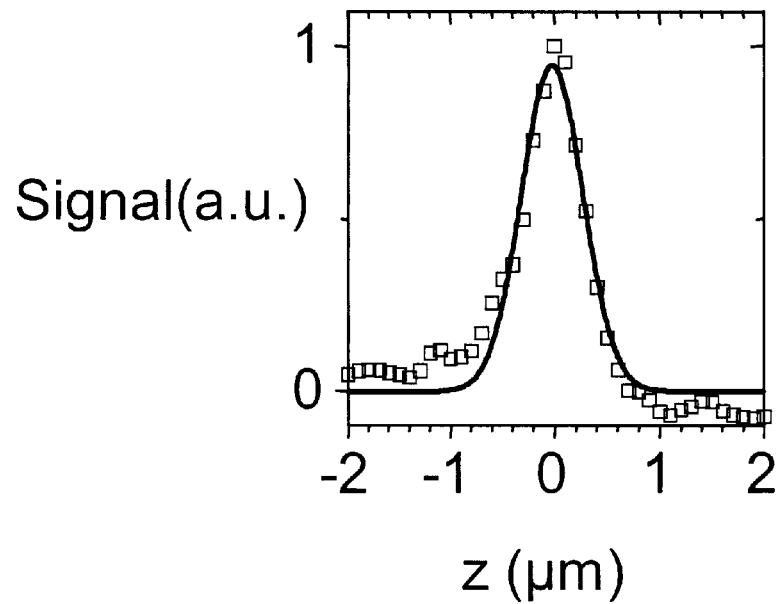

The transverse and axial resolutions of the method and device of the invention result from a combination of the size of the heating laser beam HB and that of the sensitive probe beam SPLB. On FIG. 5A the sampled image of a 10 nm a gold colloid embedded in a PVA film (few tens of nm thick) spin-coated on a glass slide is shown. The measured resolutions along the X and Y reference directions is 217±5 nm (FWHM), from a Gaussian fit, which is comparable to the transverse size of the focussed heating laser beam $dx=1.22\lambda_{green}/2NA=224$ nm. In this configuration, the size of sensitive probe laser beams does not play a role as they only fill ⅔ of the back aperture of the objective. Their transverse sizes, about $1.22\lambda_{probe}/(2(\frac{2}{3})NA)$ at about 410 nm, are thus greater than that of the heating laser beam. On the contrary, in a wide field configuration where the heating laser beam HB profile is uniform over the field of view, the heating laser beam having been defocused, the measured transverse resolution (460±25 nm FWHM) compares very well to the size of the sensitive laser beams. Finally, the measured axial resolution along the Z reference method and device of the invention, with a well focused heating beam, is 1.2±0.2 µm (FWHM, see FIG. 5B), in good accordance with the theoretical axial size of the heating beam, $1.22\lambda_{green}/NA^2 = 1.0$ µm. The measured spot along the Z-axis was, however, not perfectly symmetrical in the conducted experiments which is a consequence of aberrations. Single nanogold particles can be hence localized with a very high pointing accuracy because the signal is stable and does not saturate. The signal to noise ratio has been evaluated above 200 which leads to a measured pointing accuracy of 7 nm in the transverse directions and 32 nm in the axial direction, far below the diffraction limit.

Phase Shift Measurement

To directly measure the phase difference or slight phase changes caused by a single nanoparticle, the heating laser beam HB was switched off and an electro-optic modulator (EOM) operating at the heating beam's modulation frequency was inserted in the telecentric system or sub-unit 1,2. The EOM was turned up to the point where a phase difference between the sensitive probe laser beam SPLB and phase reference laser beam φLB giving rise to a demodulated signal equals to that of a single nanoparticle actually appeared. The measured phase difference was equal to $1(+0.5) \times 10^{-5}$ red.

Immunohistochemistry Assay

Figure 6A:
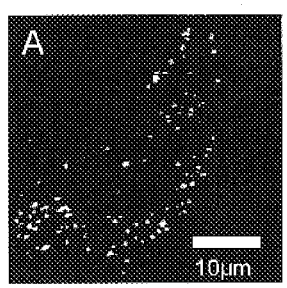
FIGS. 6A to 6C show sliced images of a living cell labeled with tiny metal particles, with the sliced images being taken along the axial direction thanks to the method and device of the invention.
Figure 6B:
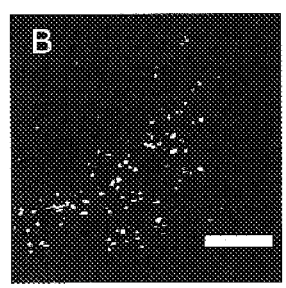
Figure 6E:
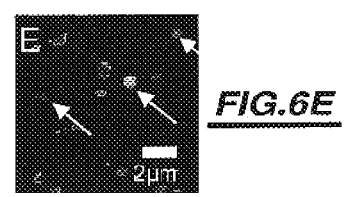
FIGS. 6E to 6G show a superimposition imaging of FIGS. 6D and 6A to 6C respectively.
Figure 6F:
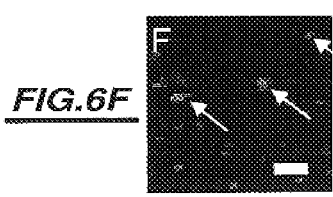
Figure 6C:
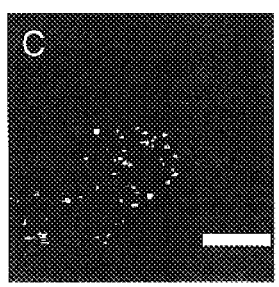
Figure 6D:
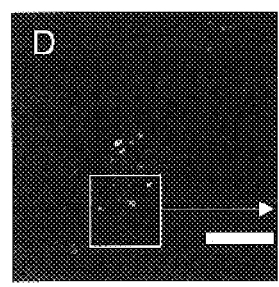
FIG. 6D shows a fluorescence imaging of the same living cell as shown at FIGS. 6A to 6C.
Figure 6G:
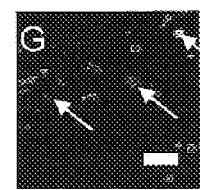

Immunohistochemistry assay has been performed to demonstrate the capabilities of the method and device of the invention to optically image immunogold labelled protein in cells. Protein conjugated colloid gold particles can be obtained commercially in sizes ranging from 1 nm to hundreds of nanometers. Electron microscopy usually prefers to use metal particles smaller than 10 nm because of their better penetration in cellular organelles. To illustrate the capability of the method and device of the invention COS7 cells were transfected, as already disclosed. Images obtained by fluorescence microscopy easily discriminate cells that contained fluorescence-labelled receptors from untransfected cells. Specificity of the gold labelling was subsequently ensured as no signal was detected by the method of the present invention on cells which did not express the proteins (non fluorescent cells, not shown). Expressing cells were thus studied as shown on FIGS. 6A to 6C and for the same cell, photothermal images are presented for different focuses separated, by 2 µm along the Z reference direction, with the heating beam power of 4.4 mW (40 µm×40 µm, 200 pixels/line, 10 ms pixel) so as to obtain sliced images. AntigG-10 nm gold labelling is clearly present on the cell. FIG. 6D is a fluorescence imaging of the same cell with its highlighted square area being superimposed to FIGS. 6A, 6B and 6C respectively to obtain FIGS. 6E, 6F and 6G. Furthermore, although the images are identical for as many scan with the same focus due to the non-photo bleaching feature of the labels, the images are different for each focus. This a consequence of the axial sectioning of the heating beam. The specificity of the gold labelling is further demonstrated by the colocalizations between antimyc-alexa labelling (fluorescence) and AntiIgG-10 nm gold labelling according to the method of the invention as indicated by arrows on FIGS. 6E to 6G. The colocalizations appear for specific focuses of the photothermal images but not in the fluorescence imaging which was not confocal in this situation. Finally, as expected, it has been controlled that the density of gold labelling is greatly reduced when lower amounts of antiIgG-10 nm gold antibodies are used.

Figure 7A:
FIGS. 7A to 7C are illustrative of the detection of one single nano-particle as a label associated to antiIgG antibodies.
Figure 7B:
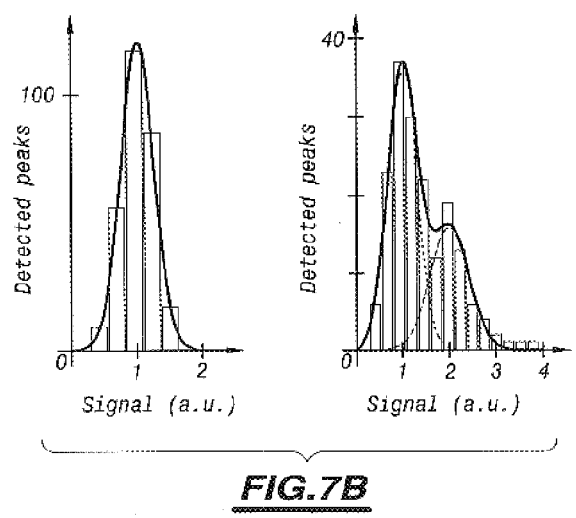
Figure 7C:
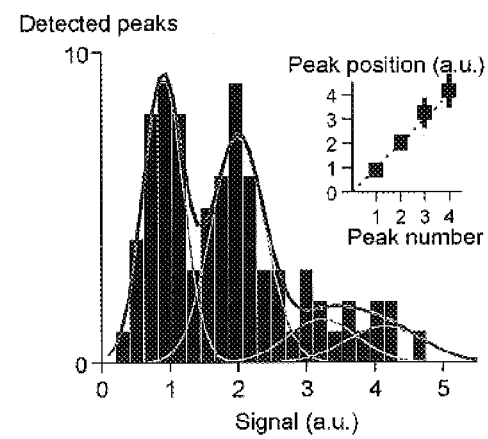

Several arguments indicate that a single 10 nm gold particle optical detection in cells has been achieved. First, when increasing the intensity of the heating laser by 5 folds, no weaker spot appeared in the image (see FIG. 7C). This indicates that the sensitivity to detect the smallest features present on the plasma membrane of the cells has been reached. Secondly, the distribution both from 10 nm gold colloids (FIG. 7B) or from the antiIgG-10 nm gold antibodies (FIG. 7C) when embedded in a PVA film a few tens of nm thick, spin-coated on a glass slide, and from peaks detected on the plasma membrane of cells labelled with diluted solutions of antiIgG-10 nm gold (FIG. 7C) were measured. The result given on FIG. 7B clearly indicate that single nanoparticles can be detected in polymers as evidenced by the narrow monomodal distribution obtained with a width equal to 0.3 (center normalized to 1). The width of the distribution stems from the dispersion (10%) of the particle which translates to 30% dispersion in the signal following the dispersion of the volume. Most notably, the distribution obtained from spin-coated antiIgG-10 nm gold antibodies is bimodal. When fitting the distribution with two Gaussian curves and normalizing the position of the first Gaussian curve to 1, the width, σ, of the first peak is found to be equal to 0.32±0.03 as previously, the position of the second peak 2.02±0.08 and its width 0.42±0.08 at around √2×σ. The position and width values of the two peaks are thus those which were expected for the signal obtained for one particle in the first peak and two particles in the second peak. One can thus come to the conclusion that antiIgG antibodies are labelled with either one (63±10%) or two 10 nm gold particles and no more than two. In order to characterize the signals obtained in the cells, the signals were analysed with the laser beams spots whose width is larger than the diffraction limit as measured. Thus doing, large aggregates of labelled receptors and out-of-focus signals were rejected. The result is visible on the histogram on FIG. 7B. The discretized distribution is well fitted by four Gaussian curves with fixed widths equal to SQRT(N)×σ, σ×√, N being the number of the peaks. Furthermore, the centres of the fitted peaks follow a linear dependence as seen on FIG. 7C. Compared to the results obtained from spin-coated antiIgG-10 nm gold antibodies, the histogram indicates that mainly single antiIgG-10 nm antibodies are detected and in the first peaks, those IgG antibodies contain are labelled with a single nanoparticle only. Altogether the data presented on FIG. 7A to 7C indicates that individual 10 nm nanoparticles are easily detected in the membrane of the cells.

The above-mentioned experiments on cell carried out thanks to the method and device of the invention demonstrated that the axial sectioning feature and sliced imaging of cell have enabled to perform 3D localization of the single gold nano-particles with very high pointing accuracy as the photothermal signal neither does photobleach nor saturate. Moreover, the method and device of the invention are able to detect individual antiIgG-10 nm gold particles in the given environment formed by a cell. The advantages over fluorescent methods at the single molecule level both stem from the absence of autofluorescence from the environment—from the cells themselves—and from the blinking and photo bleaching of the fluorophores. The latter limitation is very restrictive to perform 3D localization of the single fluorescent molecules as multiple records of the same molecules are hardly feasible. The durability of the photothermal signal and the absence of environmental noise make the method and device of the invention a first-choice way to perform single nano-particle detection in the cells.

It has also been demonstrated that the method and device of the invention allow an accurate and robust method to perform stoechiometry of gold nanoparticles. The number of present on IgG antibodies was found to amount to one or two. It certainly would have been surprising to obtain more than two 10 nm gold colloids on a single IgG antibody due to steric limitations knowing that the typical size of a Fc fragment reaches an average of 10–15 nm. Clearly this capacity to perform robust and non-transcient stoechiometry measurements appears to be extremely helpful to quantify amounts of proteins in cells but also on biotechnical assays or protein chips.

The experiments have also demonstrated that 10 nm particles used commonly to label proteins in cells can be optically detected in ambient conditions. By using a full optical method, they can be detected at the single particle level with a 3D information on their localisation. The transverse and axial resolution of the method and device of the invention which is given by the dimensions of the focused heating beam has been measured. It has the potential to attain the resolutions obtained by confocal fluorescence microscopes (SQRT (2) i.e. $\sqrt{2}$) improvement but is most unlikely to attain those of more sophisticated techniques. Nevertheless, the method and device of the invention have an edge over fluorescence methods to provide a way to localise in 3D single particles with a number of recordings and signal levels which can be arbitrary high. Indeed neither photo bleaching nor saturation of the signal exists. Single nanoparticles can thus be localized in the 3D environment of the cells with any desired precision.

What is claimed is:

1. A method for photothermal imaging tiny metal particles immersed in a given medium said given medium being deposited onto a transparent glass slide, said method comprising at least:

illuminating said given medium and immersed tiny particles through separate phase reference laser beam and sensitive probe laser beam, said sensitive probe laser beam undergoing through impingement of said sensitive probe laser beam on said given medium slight phase changes induced by photothermal effect due to a local heating within said given medium in the absence of any substantial phase changes to said phase reference laser beam, said illuminating consisting in focusing said separate phase reference laser beam and sensitive probe laser beam through said transparent glass slide at a given depth within said given medium from the output face of said transparent glass slide, so as to generating thus a transmitted phase reference laser beam and a transmitted sensitive probe laser beam undergoing said slight phase changes induced by photothermal effect due to a local heating, forming an image of said, given medium and tiny particles at said given depth through said transmitted phase reference laser beam and sensitive probe laser beam, detecting said slight phase changes on said transmitted sensitive probe laser beam with reference to said transmitted phase reference laser beam on said image through differential phase interference contrast phenomenon, thereby allowing each of said tiny metal particles immersed in said given medium to be imaged as an optical label.

2. The method of claim 1, wherein illuminating said given medium and immersed tiny particles comprises:

splitting a probe laser beam into a first and second probe laser beam, said first and second probe laser beam undergoing the same phase relationship on separate optical paths;

superimposing on one of said first and second probe laser beam a heating laser beam propagating on the same optical path as that of said one of said first and second probe laser beam on which it is superimposed, said one of said first and second probe laser beam and superimposed heating laser beam forming said sensitive probe laser beam and the other of said one of said first and second probe laser beam forming said phase reference laser beam.

3. The method of claim 2, said method further including:

amplitude modulating said heating laser beam at a given frequency; and synchronously detecting said slight phase changes through differential phase interference contrast phenomenon.

4. The method of claim 3, in which said given frequency is executed at a frequency between 100 kHz and 10 MHz, said frequency being such that a given volume of said given medium overlaps the focal spot of said sensitive probe laser beam focused on said given medium.

5. The method of claim 1, wherein detecting said slight phase changes on said transmitted sensitive probe laser beam with reference to said transmitted phase reference laser beam on said image comprises:

retro-reflecting said image and transmitted sensitive probe laser beam and phase reference laser beam forming said image;

recombining said retro-reflected transmitted phase reference laser beam and sensitive probe laser beam into a unique sensing laser beam in which said differential phase interference phenomenon is induced.

6. The method of claim 1, wherein said step of focusing said separate phase reference laser beam and sensitive probe laser beam is performed by successive shifting increments along two reference directions parallel to the output face of said transparent glass slide at a same given depth within said given medium, thereby allowing a two dimensional imaging of said given medium and tiny particles thereof at said given depth to be obtained.

7. The method of claim 1, wherein said step of focusing said separate phase reference laser beam and sensitive probe laser beam at a given depth is performed by successive depth increments from the output face of said transparent glass slide, thereby allowing a sliced imaging of said given medium and tiny particles thereof at successive intermediate depths to be obtained.

8. The method of claim 1, wherein said step of focusing said phase reference laser beam and sensitive probe laser beam further includes:

focusing at least a first and a second set of phase reference laser beam and sensitive probe laser beam, the beam centers of the laser beams of said first and second set of phase reference and sensitive probe laser beam being oriented so as to define a first and a second reference directions in a plane in which the laser beams forming said first and second set of phase reference and sensitive probe laser beam are focused;

forming an image of said given medium and tiny particles thereof which are located in between said first and second set of phase reference and sensitive probe laser beam, thereby allowing any of said tiny particles to be imaged and located with respect to said first and second reference directions.

9. The method of claim 8, wherein the heating laser beam which is superimposed onto said one of said first and second probe laser beam of said first and second set of phase reference and sensitive probe laser beam are slightly defocused, so as to substantially cover the central area of said given medium lying between the phase reference and sensitive probe laser beams forming said first and second set.

10. The method of one of claim 1, in which said tiny metal particles are nanometer particles.

11. A device for photothermal imaging of tiny metal particles immersed in a given medium, said device comprising at least:

means for illuminating part of said given medium and immersed tiny particles through separate phase reference laser beam and sensitive probe laser beam so as to generate transmitted sensitive probe laser beam and phase reference laser beam, said transmitted sensitive probe laser beam undergoing through impingement of said sensitive probe laser beam on said given medium slight phase changes induced by photothermal effect due to a local heating within said given medium in the absence of any substantial phase changes to said transmitted phase reference laser beam;

means for detecting said slight phase changes on said transmitted sensitive probe laser beam with reference to said transmitted phase reference laser beam through a differential phase interference contrast phenomenon;

means for imaging each of said tiny metal particles immersed in said given medium as an optical label from said differential phase interference contrast phenomenon.

12. The device of claim 11, in which said means for illuminating comprises at least:

a probing laser generator adapted to generate a probe laser beam;

means for splitting said probe laser beam to a first and a second probe laser beam, said first and second probe laser beam undergoing the same phase relationship on separate optical paths;

means for generating a heating laser beam;

means for superimposing said heating laser beam on one of said first and second probe laser beam with the superimposed heating laser beam propagating on the same optical path as that of said one of said first and second probe laser beam onto which it is superimposed, said superimposed heating laser beam and one of said first and second probe laser beam propagating onto the same optical path thus constituting said sensitive probe laser beam and the other of said one of said first and second probe laser beam separate from said same optical path constituting said phase reference laser beam;

means for focusing said phase reference laser beam and said sensitive probe laser beam at separate location on said given medium.

13. The device of claim 12, in which for a given medium deposited on a transparent glass slide, said device further includes at least:

a 3D moving table, in given reference directions, two of said reference directions being substantially parallel to the input face of said transparent glass slide and the third one of said reference directions being substantially perpendicular to the input and output face of said transparent glass slide;

an objective lens mounted onto said 3D moving table, said objective lens and 3D moving table being thus adapted to focusing said separate reference laser beam and sensitive probe laser beam through said transparent glass slide at a given depth within said given medium from the output face of said transparent glass slide;

focusing means for forming an image of said given medium and tiny particles at said given depth through any transmitted phase reference laser beam and sensitive probe laser beam undergoing said slight phase changes induced by photothermal effect due to a local heating emerging from said given medium.

14. The device of claim 13, further including downstreams said focusing means for forming an image of said given medium and tiny particles at said given depth, means for retro-reflecting said transmitted sensitive probe laser beam and phase reference laser beam along corresponding optical paths of said sensitive probe laser beam and phase reference laser beam illuminating said given medium; and upstreams said focusing means for forming an image of said given medium and tiny particles at said given depth, means for recombining said retro-reflected transmitted phase reference and sensitive probe laser beam to a unique laser beam in which said differential phase interference phenomenon is induced.

15. The device of claim 11, wherein said means for detecting said slight phase changes onto said deflected sensitive probe laser beam comprise at least:

means for focusing back said reflected phase reference laser beam and reflected sensitive probe laser beam along corresponding optical paths of said first and second probe laser beam;

means for recombining said focused reflected phase reference and reflected sensitive probe laser beam to a unique sensing laser beam in which said differential phase interference phenomenon is induced.

16. The device of claim 11, wherein said means for superimposing, said means for focusing and said means for focusing back are common so as to form a telecentric system.

17. The device of claim 11, wherein said means for splitting and said means for recombining are common and include a polarizing cube and a Wollaston prism.

18. A method for photothermal imaging tiny metal particles immersed in a given medium said given medium being deposited on a transparent glass slide, said method comprising at least:

illuminating said given medium and immersed tiny particles through separate phase reference laser beam and sensitive probe laser beam, said sensitive probe laser beam undergoing through impingement of said sensitive probe laser beam on said given medium slight phase changes induced by photothermal effect due to a local heating within said given medium in the absence of any substantial phase changes to said phase reference laser beam, said illuminating consisting in focusing said separate phase reference laser beam and sensitive probe laser beam through said transparent glass slide at a given depth within said given medium from the output face of said transparent glass slide, so as to generating thus a transmitted phase reference laser beam and a transmitted sensitive probe laser beam undergoing said slight phase changes induced by photothermal effect due to a local heating, forming an image of said given medium and tiny particles at said given depth through said transmitted phase reference laser beam and sensitive probe laser beam, detecting said slight phase changes on said transmitted sensitive probe laser beam with reference to said transmitted phase reference laser beam on said image through differential phase interference contrast phenomenon, thereby allowing each of said tiny metal particles immersed in said given medium to be imaged as an optical label for cell membrane proteins labeling.

19. A method for photothermal imaging tiny metal particles immersed in a given medium said given medium being deposited onto a transparent glass slide, said method comprising at least:

illuminating said given medium and immersed tiny particles through separate phase reference laser beam and sensitive probe laser beam, said sensitive probe laser beam undergoing through impingement of said sensitive probe laser beam on said given medium slight phase changes induced by photothermal effect due to a local heating within said given medium in the absence of any substantial phase changes to said phase reference laser beam, said illuminating consisting in focusing said separate phase reference laser beam and sensitive probe laser beam through said transparent glass slide at a given depth within said given medium from the output face of said transparent glass slide, so as to generating thus a transmitted phase reference laser beam and a transmitted sensitive probe laser beam undergoing said slight phase changes induced by photothermal effect due to a local heating, forming an image of said given medium and tiny particles at said given depth through said transmitted phase reference laser beam and sensitive probe laser beam, detecting said slight phase changes on said transmitted sensitive probe laser beam with reference to said transmitted phase reference laser beam on said image through differential phase interference contrast phenomenon, thereby allowing each of said tiny metal particles immersed in said given medium to be imaged as an optical label for 3D tracking.

20. The device of claim 12, wherein said means for superimposing, said means for focusing and said means for focusing back are common so as to form a telecentric system.

21. The device of claim 12, wherein said means for splitting and said means for recombining are common and include a polarizing cube and a Wollaston prism.

* * * * *